United States Patent
Sunday et al.

(10) Patent No.: US 9,237,976 B2
(45) Date of Patent: Jan. 19, 2016

(54) FLUID ABSORPTION AND DISTRIBUTION ENHANCEMENT SYSTEMS

(71) Applicant: Cornerstone Research Group, Inc., Dayton, OH (US)

(72) Inventors: Matthew B. Sunday, Demossville, KY (US); Joseph H. Althaus, Yellow Springs, OH (US); Brian E. Henslee, Galloway, OH (US); Benjamin C. MacMurray, Bellbrook, OH (US)

(73) Assignee: Cornerstone Research Group, Inc., Dayton, OH (US)

( * ) Notice: Subject to any disclaimer, the term of this patent is extended or adjusted under 35 U.S.C. 154(b) by 366 days.

(21) Appl. No.: 13/834,239

(22) Filed: Mar. 15, 2013

(65) Prior Publication Data

US 2014/0208516 A1    Jul. 31, 2014

Related U.S. Application Data

(60) Provisional application No. 61/758,524, filed on Jan. 30, 2013.

(51) Int. Cl.
| | |
|---|---|
| *B01J 20/26* | (2006.01) |
| *A61G 1/04* | (2006.01) |
| *A61F 13/49* | (2006.01) |
| *A61F 13/534* | (2006.01) |
| *A61F 13/537* | (2006.01) |
| *A61F 13/532* | (2006.01) |
| *A61F 13/536* | (2006.01) |
| *A61F 13/53* | (2006.01) |

(52) U.S. Cl.
CPC ............ *A61G 1/04* (2013.01); *A61F 13/49001* (2013.01); *A61F 13/534* (2013.01); *A61F 13/536* (2013.01); *A61F 13/537* (2013.01); *A61F 13/5323* (2013.01); *A61F 2013/53062* (2013.01); *A61F 2013/530554* (2013.01); *Y10T 137/0318* (2015.04)

(58) Field of Classification Search
CPC ....................................................... B01J 20/26
USPC ......................................................... 502/402
See application file for complete search history.

(56) References Cited

U.S. PATENT DOCUMENTS

| | | |
|---|---|---|
| 5,713,372 A | 2/1998 | Pinney et al. |
| 8,142,410 B2 | 3/2012 | Rovaniemi |
| 2003/0082966 A1 | 5/2003 | Menday et al. |
| 2003/0135177 A1 | 7/2003 | Baker |
| 2003/0135178 A1 | 7/2003 | Hansen |
| 2006/0069375 A1 | 3/2006 | Waksmundzki et al. |
| 2011/0190720 A1 | 8/2011 | Skreosen |
| 2012/0053545 A1 | 3/2012 | Love et al. |
| 2012/0284923 A1 | 11/2012 | Jensen et al. |

FOREIGN PATENT DOCUMENTS

WO    01/21873 A1    3/2001

OTHER PUBLICATIONS

European Search Report dated Apr. 3, 2014 pertaining to European Patent Application No. 13194956.2.

*Primary Examiner* — Edward Johnson
(74) *Attorney, Agent, or Firm* — Dinsmore & Shohl LLP

(57) ABSTRACT

Embodiments of a fluid absorption and distribution enhancement (FADE) product comprises at least one flow media layer, and at least one superabsorbent polymer layer.

20 Claims, 9 Drawing Sheets

FLUID ABSORPTION AND DISTRIBUTION ENHANCEMENT SYSTEMS

CROSS REFERENCE TO RELATED APPLICATIONS

This application claims priority to U.S. Provisional Application Ser. No. 61/758,524 filed Jan. 30, 2013, which is incorporated by reference herein in its entirety.

STATEMENT REGARDING FEDERALLY SPONSORED RESEARCH OR DEVELOPMENT

This invention was made with U.S. Government support under Contract No. W81XWH-10-C-0193 awarded by the United States Army Medical Research and Material Command to Cornerstone Research Group Inc. The U.S. Government has certain rights in the invention.

BACKGROUND

Patients being transported with significant injuries can expose the transport equipment and caregivers to copious amounts of body fluids, e.g., urine, blood, feces, etc. Therefore, management of these fluids is important for proper patient treatment, reduced infection, and easier decontamination. Additionally, for long term transport scenarios, it reduces the likelihood of pressure ulcer development.

Conventional products have utilized superabsorbent polymers to absorb these body fluids; however, conventional products encounter various deficiencies and limitations, such as gel blocking due to engorged superabsorbent polymers, poor absorbency under load, poor fluid distribution across the superabsorbent polymer, slow absorption rates and poor absorption capacity, as well as an inability to meet dimensional constraints and maintain the structural integrity of the superabsorbent polymer.

Regarding dimensional constraints, conventional products fail to achieve good fluid distribution to all regions of an absorbent pad. Therefore, these products compensate by adding more superabsorbent polymer material making the end product thicker or bulkier. This is undesirable in many applications such as adult diapers where discretion is important. In these applications, wherein the product is thicker than desired because of poor fluid distribution, gel blocking, and absorption under load issues. Moreover, structural integrity of the envelope or containment pouch for the absorbent pad can rupture due to excessively engorged superabsorbent polymer in regions that have poor fluid distribution.

SUMMARY

Figure 1:
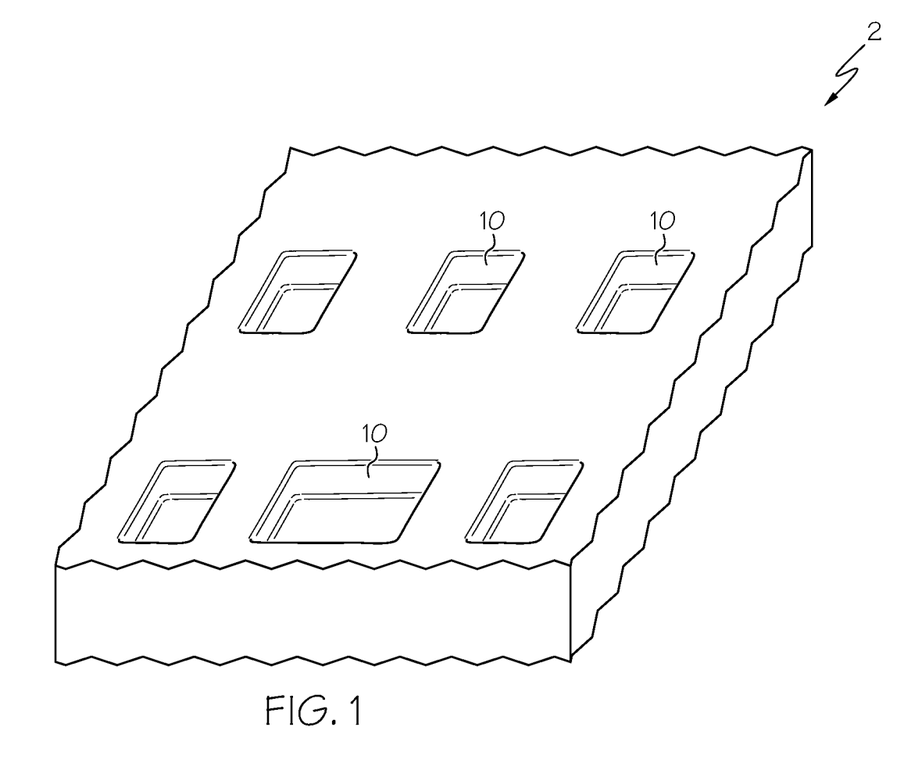
FIG. 1 is a picture of a patient support litter including fluid drainage cutouts.
Figure 2:
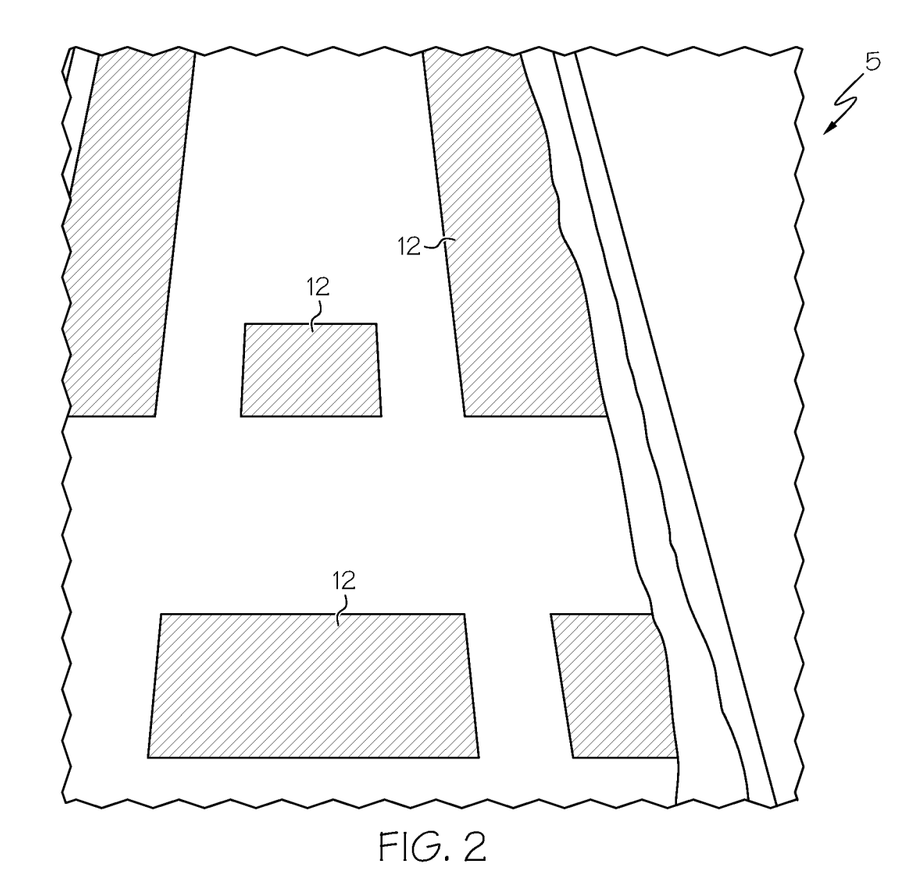
FIG. 2 is a picture of the present fluid absorption and distribution enhancement product according to one or more embodiments of the present invention.

Accordingly, the present inventors have developed a new fluid management system (hereinafter "fluid absorption and distribution enhancement product" or FADE product) to achieve improved fluid management, especially for conventional patient transport litters, stretchers, hospital beds, or ambulance cots. In addition to absorption of body fluids, non-body fluids, for example, fluids used for patient treatment (e.g., sterile water used for irrigating burn wounds). Referring to the embodiment of FIGS. 1 and 2, the present FADE product 5 (shown in FIG. 2) can underlie a conventional mattress 2, for example a mattress used on a patient support litter. As shown in FIG. 1, the mattress 2 includes drainage slots 10 which act as flow channels for bodily fluids to pass through the mattress 2. As shown in FIG. 2, the present FADE product may include drainage channels 12 configured to align with the drainage slots 10 when disposed under the mattress of FIG. 1. In operation, bodily fluids will travel through the drainage slots and be collected and absorbed within the present FADE product, which includes a system of flow channels and adsorbent materials. The present FADE product may be a disposable layered pad comprised of wicking and adsorbent materials developed for bulk fluid trapping and removal. While the present fluid absorption product is useable with any conventional mattress, it is contemplated that a mattress could be optimized as well to provide improved channeling for drainage and fluid management in conjunction with the present fluid absorption product.

Without being limited by theory, the present FADE product has the ability to drain, channel, and evenly disperse bodily fluid under a load force or under vacuum while preventing gel blocking at the fluid introduction location, which is prevalent in superabsorbent polymer applications.

While many of the embodiments discussed herein are focused on patient transport litters, stretchers, hospital beds, or ambulance cots, the present fluid absorption product is suitable generally for use in absorption pads (for example, absorption pads for the medical, pet, and food industries), medical dressings, diapers, and any other application where fluid distribution and/or absorption is desired.

Without being bound by theory, the present FADE product achieves numerous benefits. For example, and not by way of limitation, these benefits include: significantly accelerated fluid absorption time; uniform distribution of fluid across absorbent pad; avoidance of gel-blocking of the absorbent pad which inhibits fluid absorption; maximized use of the superabsorbent polymer material; ultrathin embodiment and dimensional control options; flow potential against gravity; significantly greater absorbance under load; an increased ability to deal with subsequent insults or incidents yielding increased bodily fluid; and anti-shear properties that allow movement within the pad instead of translating into the patient's soft tissue.

In accordance with one embodiment, the FADE product comprises at least two flow media layers, and at least one superabsorbent polymer layer sandwiched between flow media layers.

Alternatively, a FADE product with a single flow media layer is also possible. For example, a fluid absorption and distribution enhancement (FADE) product comprises at least one flow media layer, wherein the superabsorbent polymer layer comprises flow channels, and at least one superabsorbent polymer layer disposed below the flow media layer (See FIG. 4), or above the flow media layer (See FIG. 5).

In accordance with another embodiment, a method of improved fluid absorption and distribution enhancement under load is provided. The method comprises providing a fluid absorption and distribution enhancement product under an applied load, wherein the fluid absorption and distribution enhancement product comprises at least two flow media layers, and at least one superabsorbent polymer layer comprising one or more flow channels extending therethrough, wherein the two flow media layers comprise an upper flow media layer and a lower flow media layer, and wherein the superabsorbent polymer layer is disposed between the upper flow media layer and lower flow media layer, and enhancing fluid distribution and fluid absorption in the superabsorbent polymer layer by draining fluid laterally by the upper flow media layer and through flow channels in the superabsorbent layer to the lower flow media layer.

In accordance with yet another embodiment, the FADE product comprises at least three flow media layers including an upper flow media layer, a middle flow media layer, and a lower flow media layer, and at least two superabsorbent polymer layers comprising a first superabsorbent polymer layer disposed between the upper flow media layer and the middle flow media layer, and a second superabsorbent layer disposed between the middle flow media layer and the lower flow media layer.

In yet another embodiment, fluid absorption and distribution enhancement (FADE) product comprising at least one flow media layer, and at least one superabsorbent polymer layer disposed above or below the flow media layer and comprising at least one flow channel.

These and additional features provided by the embodiments of the present disclosure will be more fully understood in view of the following detailed description, in conjunction with the drawings.

BRIEF DESCRIPTION OF THE DRAWING

The following detailed description of specific embodiments of the present disclosure can be best understood when read in conjunction with the drawings enclosed herewith.

The embodiments set forth in the drawings are illustrative in nature and not intended to be limiting of the invention defined by the claims. Moreover, individual features of the drawings will be more fully apparent and understood in view of the detailed description.

DETAILED DESCRIPTION

Figure 4:
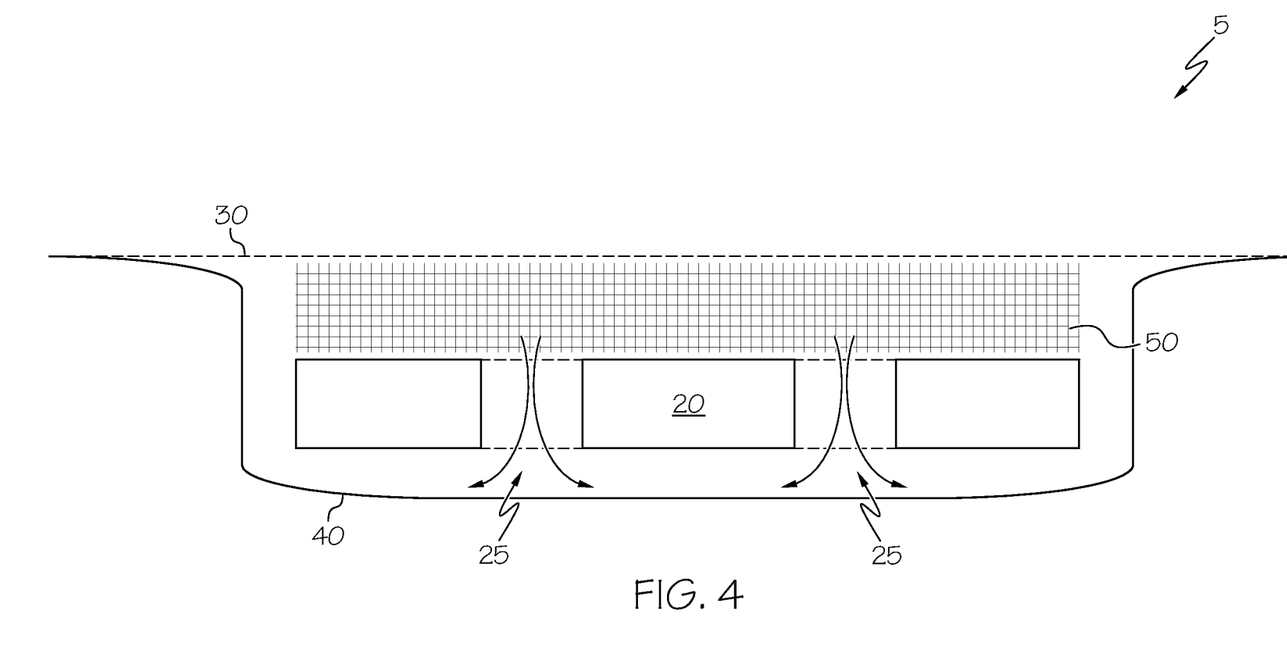
FIG. 4 is a schematic view of a fluid absorption and distribution enhancement product having a channeled single superabsorbent polymer layer and a flow media layer thereon according to one or more embodiments of the present invention.
Figure 5:
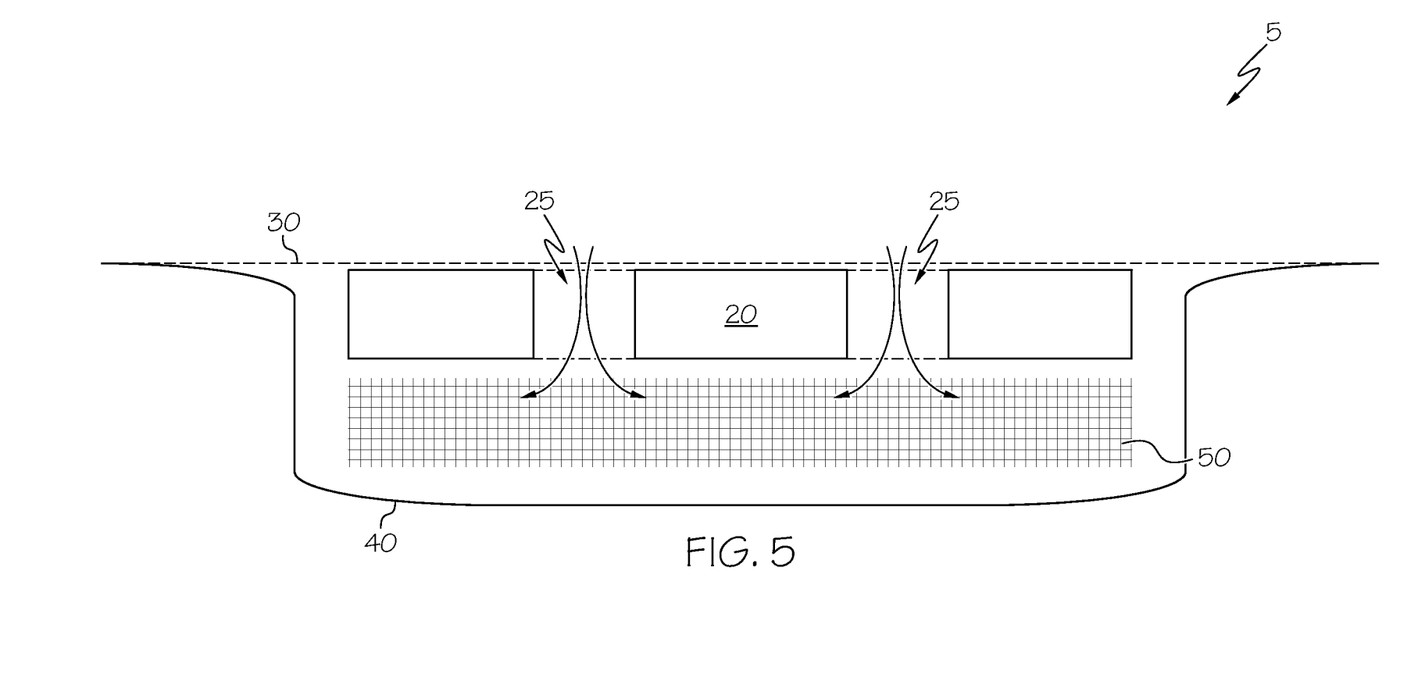
FIG. 5 is a schematic view of another fluid absorption and distribution enhancement product having a channeled single superabsorbent polymer layer and a flow media layer disposed below the channeled single superabsorbent polymer according to one or more embodiments of the present invention.
Figure 6:
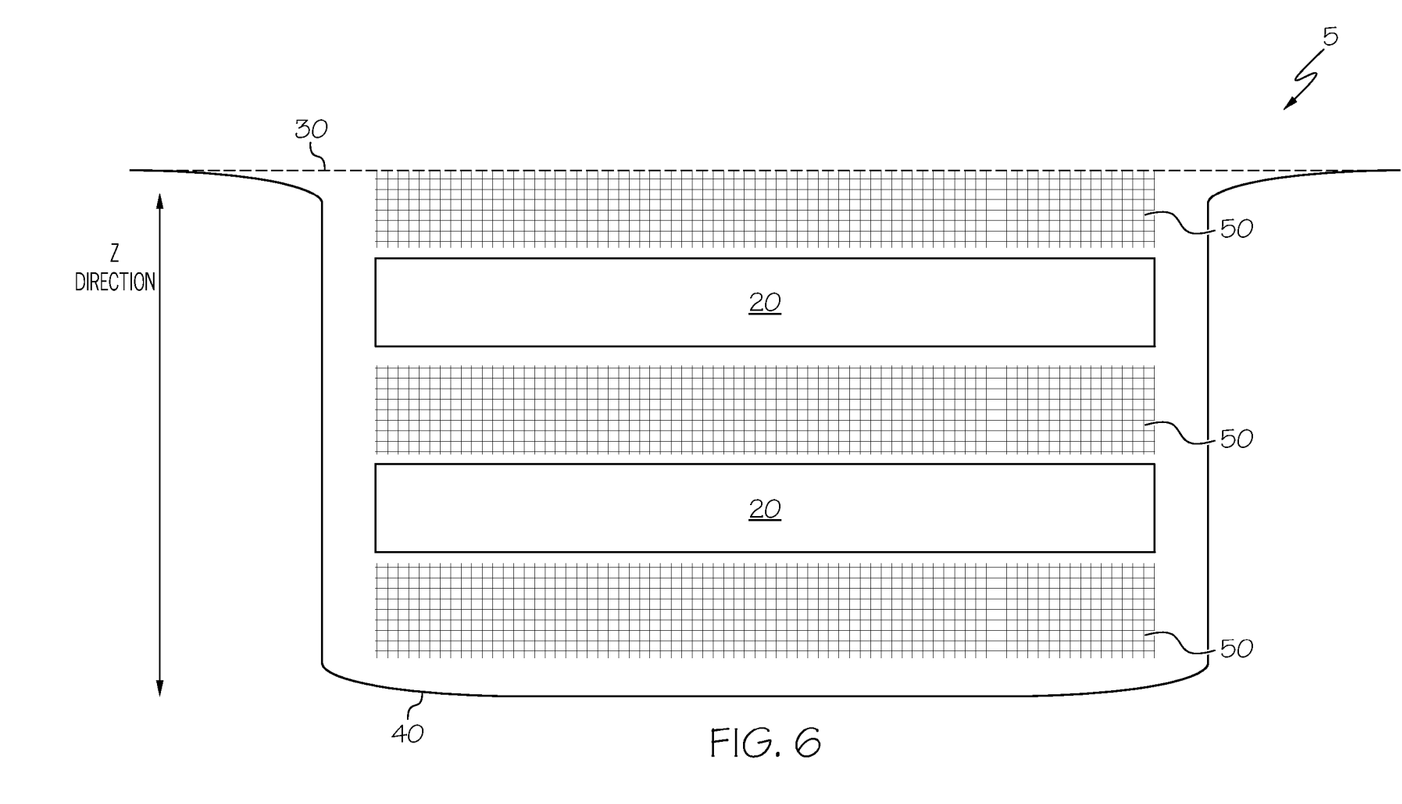
FIG. 6 is a schematic view of a multi-layer fluid absorption and distribution enhancement product according to one or more embodiments of the present invention.
Figure 7:
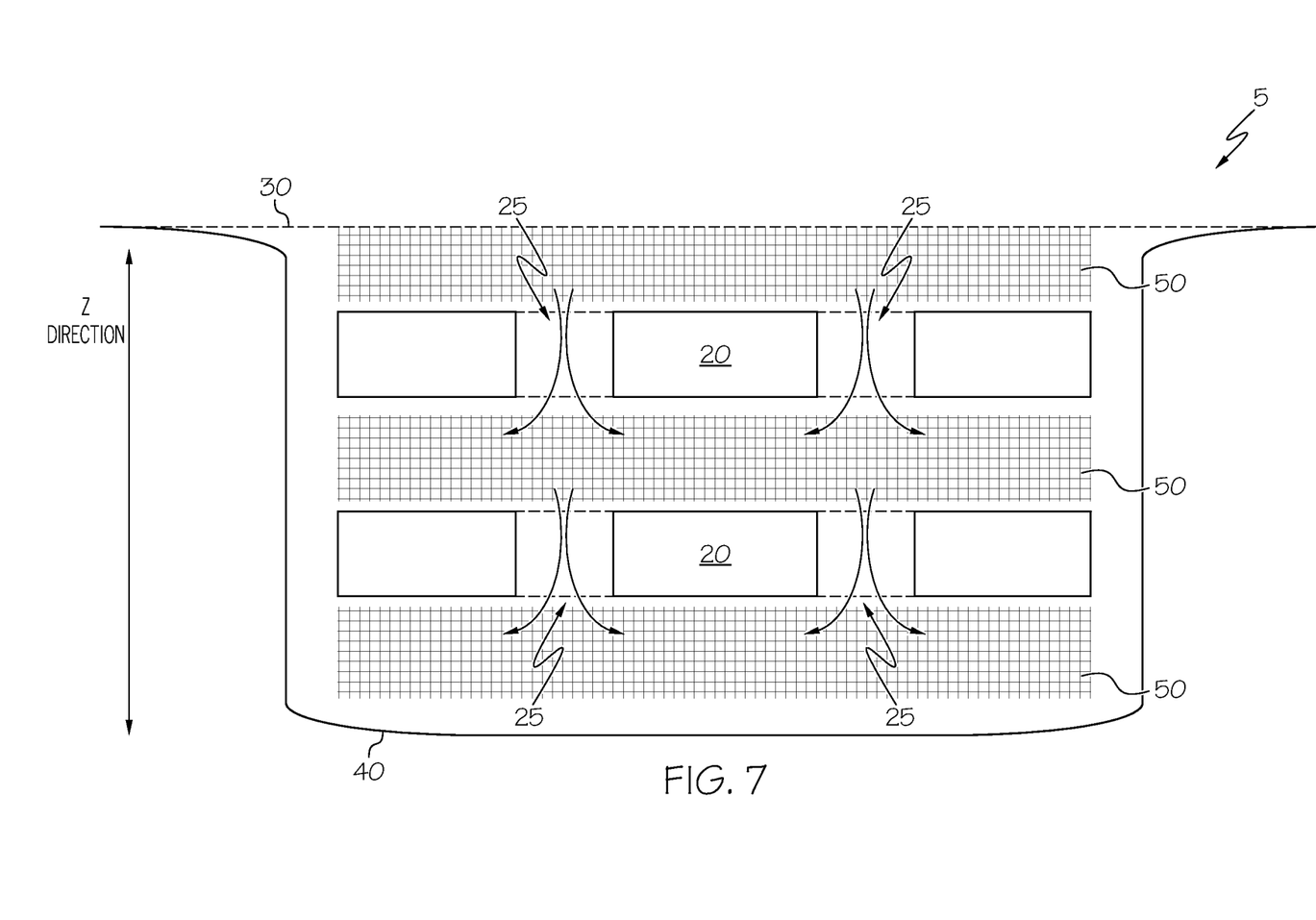
FIG. 7 is a schematic view of a multi-layer fluid absorption and distribution enhancement product having flow channels in multiple superabsorbent layers according to one or more embodiments of the present invention.

Referring to FIGS. 4-8, various embodiments of a fluid absorption and distribution enhancement (FADE) product 5 are provided. Referring to FIGS. 4 and 5, a FADE product 5 may comprise at least one flow media layer 50, and at least one superabsorbent polymer layer 20 oriented above (FIG. 4) or below (FIG. 5) the flow media layer 50, wherein the one superabsorbent polymer layer 20 includes flow channels 25 therein which assists in the lateral distribution of fluid as shown schematically in FIG. 9. Referring to FIG. 6, the FADE product 5 may comprise at least two flow media layers 50, and at least one superabsorbent polymer layer 20 sandwiched between flow media layers or adjacent flow media layer.

The ability to use multiple layers dramatically improves fluid channeling and accelerates the fluid absorption time allowing for more even fluid distribution; however, improvements in fluid distribution are achievable with various structures as well as structural modifications. For example, achieving slower or faster superabsorbent polymer absorption rates at specific layers and locations of the FADE product may be tailored by varying the layer structure as well as the channeling and drainage within the layers. Suitable contemplated structures may include, for example and not by way of limitation, single or multiple superabsorbent polymer layers, single or multiple flow media layers disposed above and/or below the superabsorbent polymer layers, and optionally superabsorbent fiber materials. As used herein "superabsorbent fiber materials" means including superabsorbent polymer in a woven or non-woven fiber structure. Various additional structures are contemplated herein, for example merely doping superabsorbent polymer onto a suitable sheet, carrier, or substrate. It is further contemplated that superabsorbent fibers may replace flow media or be used in conjunction with flow media layers.

As shown in FIGS. 4-8, the FADE product 5 may also comprise a cover layer 30. In one exemplary embodiment, the cover layer 30 comprises nonwoven mesh. Moreover as shown in FIGS. 4-8, the FADE product 5 may further comprise a backing layer 40, for example, a clear backing layer. Various additional compositions are contemplated for the cover layer 30 and backing layer 40, and it is noted that one or both of these layers is optional depending on the industrial application.

Flow media layer 50 options are vast in design, material, and dimension. For example, there are stretchy materials, varied thicknesses, coarseness, planer, and egg crate concepts that can be conceived following a review of currently available flow media and desired performance requirements. Specific tailorable performance features include the use of non-uniform, non-traditional weaves or interlacing that creates a specific flow network or pattern. Similar to the circulatory system of the human body that is comprised of arteries, arterioles, and capillaries, a network of larger to smaller channels can be created through the use of thicker material in areas where significant flow is desired. These larger pathways will quickly guide fluid to the smaller channels to allow for collection in the desired absorption zones of the pad.

In specific embodiments, the flow media layers 50 may be layers comprised of woven material such as Style 6781 S2-Glass fabric from Fibre Glast, or non-woven materials. Examples of non-woven materials that can be used as flow media layers are knit material e.g. Breatherflow 60 from Airtech, pressed directional materials, such as Resinflow 60 from Airtech, random mats, such as Continuous Strand Mat from Fibre Glast, as well as other mesh or scrim material, or combinations thereof. Another commercially suitable embodiment is the GREENFLOW 75 produced by Airtech Advanced Materials Group. Various compositions are contemplated for use in the woven or non-woven structures. For example, the flow media layers 50 may comprise nylon, polypropylene, propylene ethylene copolymer, or combinations thereof. Moreover, the flow media layers may comprise at least about 25%, or at least about 50% by weight of nylon, polypropylene, propylene ethylene copolymer, or both.

In an additional embodiment, the FADE product 5 may comprise at least two flow media layers 50 in contact with one another. Without being bound by theory, pressure, temperature, moisture, and shear all contribute to the formation of pressure ulcers for the patient. Studies show that bed sores are caused by friction and shear forces generated from movement of soft tissue around a bony contact area. To combat this shear effect, the FADE product may use two layers of flow layer media mesh in contact with one another to create a "slip sheet" allowing the absorption pad to stretch and move, instead of the patient's soft tissue, thereby reducing the likelihood of pressure ulcer development. It is contemplated that the same flow media layer compositions may be disposed in contact or different flow media layer compositions may be stacked.

As shown in FIGS. 4-8, these flow media layers 50 are porous structures, which may optionally include channels that encourage lateral fluid flow across the surface of the superabsorbent polymer layer 20. As shown in FIGS. 2, 4, and 6-8, the superabsorbent polymer layers 20 may comprise flow channels 25 extending through the superabsorbent polymer layers 20 which also encourage lateral fluid flow.

Figure 3:
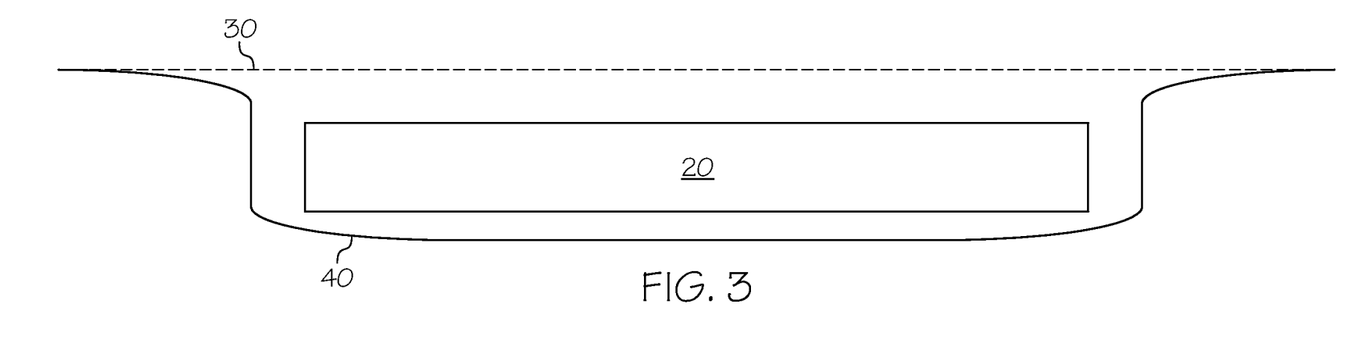
FIG. 3 is a schematic view of a commercial fluid absorption product having a single superabsorbent polymer layer.

Referring to the embodiment of FIGS. 5-8, the superabsorbent polymer layer 20 may be disposed between two flow media layers 50. Various compositions are contemplated for use as a superabsorbent polymer layer 20. For example, the superabsorbent polymer layer 20 may comprise poly (sodium acrylate) homopolymers or copolymers, polyacrylamide copolymers, ethylene maleic anhydride copolymers, polyvinyl alcohol copolymers, polyethylene oxides, polyacrylonitrile copolymers, cross-linked carboxymethylcellulose, or combinations thereof. In one exemplary embodiment, the superabsorbent polymer layer 20 comprises poly (sodium acrylate) homopolymer. Commercially suitable embodiments may include the ULTRABLEND 345 produced by Gelok International Corp. Various structural configurations are contemplated for the superabsorbent polymer layer. For example as shown in FIG. 3, the superabsorbent polymer core layer 20 may comprise a cover layer 30 on top of the superabsorbent core layer 20, and a backsheet layer 40 disposed underneath the superabsorbent core layer 20.

In further embodiments, the superabsorbent polymer layer 20 may include flow channels 25, for example, in one or more of the superabsorbent polymer layers 20 of a multi-layer FADE product 5. Specifically referring to FIGS. 7 and 8 in conjunction with FIGS. 1 and 2, these flow channels 25 may be designed cut-out areas in one or both of the superabsorbent polymer layers 20 which may be aligned with drainage slots 10 or "through holes" in the mattress 2 to further increase the z-direction flow in those areas where large amounts of fluids would be introduced to the absorbent pad and tend to pool. The ability to allow fluid movement in the z-direction as shown in FIGS. 4-8, perpendicular to the superabsorbent polymer layer 20 surface, dramatically improves fluid absorption time, provides for better fluid distribution, and can prevent gel blocking. While FIGS. 7 and 8 both show embodiments where the top or upper superabsorbent polymer layer includes flow channels 25, it is contemplated in further embodiments to only include flow channels in a lower superabsorbent polymer layer. Moreover, it is contemplated that the layers of the structure could be rearranged, so that superabsorbent polymer layers are in direct contact or the flow media layers are in direct contact.

Additionally, the FADE product 5 may comprise deionizing material or a deionizing coating. Constructing the flow media layers 30 with a deionizing material or applying a deionizing coating onto the superabsorbent polymer layer 20 can increase absorption rate as comparing to the absorption rate of ionized body fluids. Selectively employing this concept can create targeted absorption areas that can be located anywhere in the absorbent field. Without being bound by theory, keeping absorption low near the areas of fluid introduction will allow for multiple uses which is a desired feature of superabsorbent polymer pads for patients.

In yet another embodiment, the superabsorbent polymer layer 20 may comprise small slits configured to facilitate stretching. Without being limited to a specific method of making, the small slits may be laser etched into the superabsorbent polymer layer. Alternatively, the superabsorbent polymer layer may be a structure wherein superabsorbent polymer is impregnated into a stretchable fabric layer. Like the anti-shear slip sheet embodiment, the stretchability of the superabsorbent polymer achieved by a superabsorbent polymer impregnated into a stretchable fabric layer may aid in the reduction of pressure ulcers.

In one advantageous embodiment, the fluid absorption and distribution enhancement product achieves excellent fluid distribution under load. As noted above, a pressure applied to absorbent pads can impede the fluid wicking and distribution and lead to fluid pooling in specific areas. This can lead to poor absorbency. Consequently, the present fluid absorption and distribution enhancement product enhances fluid absorption in the superabsorbent polymer layer by distributing fluids through the flow media layers, and optionally may further enhance fluid absorption by including flow channels in one of the superabsorbent polymers layers, for example, in an upper superabsorbent polymer layer to allow lateral distribution of fluid into the lower superabsorbent polymer layer.

EXAMPLES

The present inventors performed comparative experiments to demonstrate that fluid absorption and distribution. The evaluations were conducted with 250 ml of saline solution 0.9% introduced through an acrylic cylinder. Absorption under load (AUL) scenarios included uniform loading using steel plates that imparted 0.15 psi on the pad surface. These AUL scenarios are used to simulate the compression created by body weight on the pad.

The starting sheet was the conventional commercial product of FIG. 3. Water and blood simulant (0.9% saline solution) were both quickly absorbed, when no load was applied.

That being said, applying pressure to the sheet of FIG. 3 impeded the ability of the sheet to absorb fluid, and fluid pool was formed. Applying pressure resulted in areas of fluid pooling as it could not wick nor absorb into the superabsorbent polymer layer. Incorporating a flow media layer 50 above the absorbent polymer 20 with flow channels 25 as shown in FIG. 4 greatly increased the wicking ability of the product and improved fluid absorption even when pressure was applied.

Incorporating two layers of superabsorbent polymer with flow media mesh layers in between resulted in improved wicking and shared absorption of fluid as shown in FIG. 6. Additionally, each superabsorbent polymer layer absorbed roughly equal quantities of the fluid.

Figure 8:
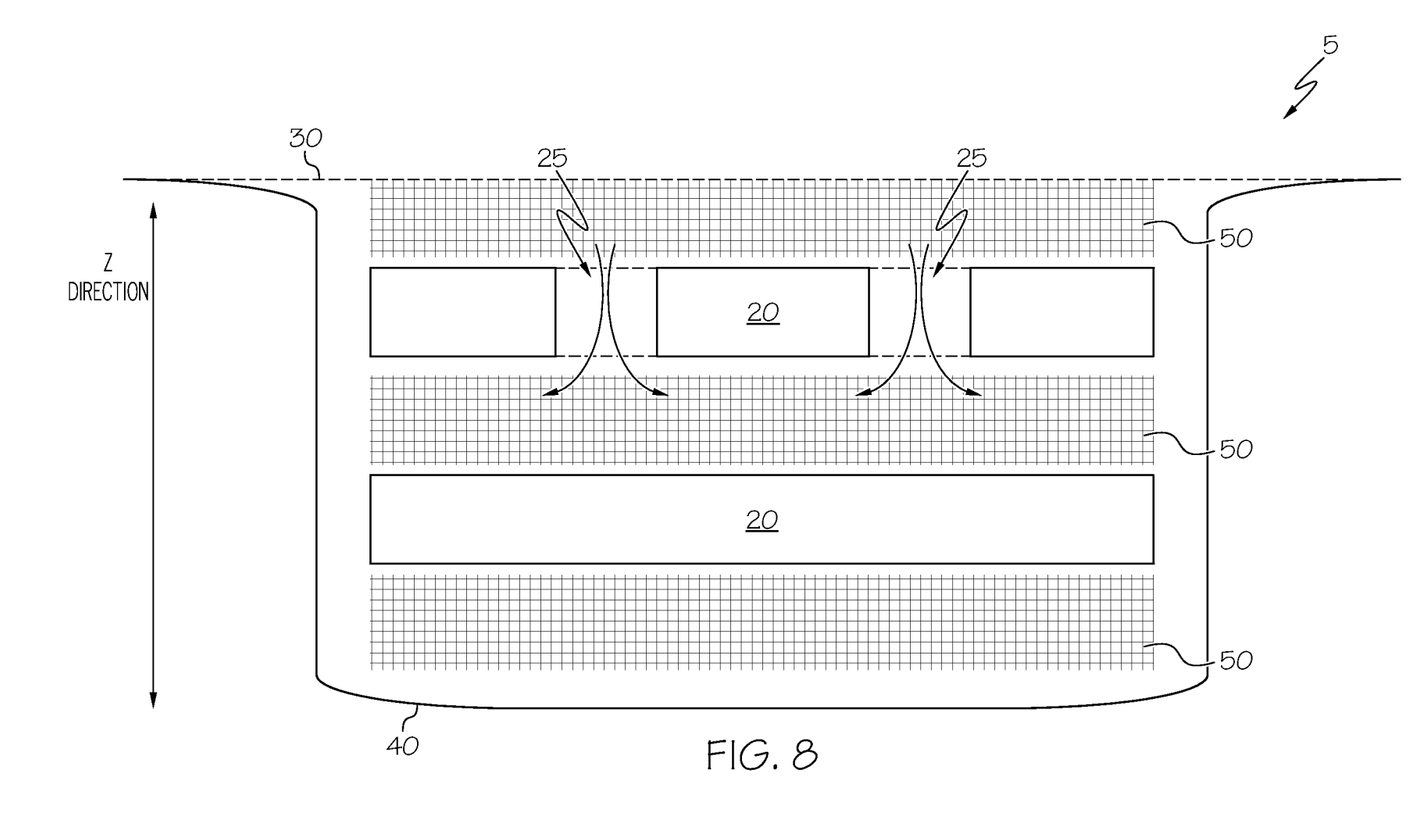
FIG. 8 is a schematic view of a multi-layer fluid absorption and distribution enhancement product having flow channels in one superabsorbent layer according to one or more embodiments of the present invention.
Figure 9:
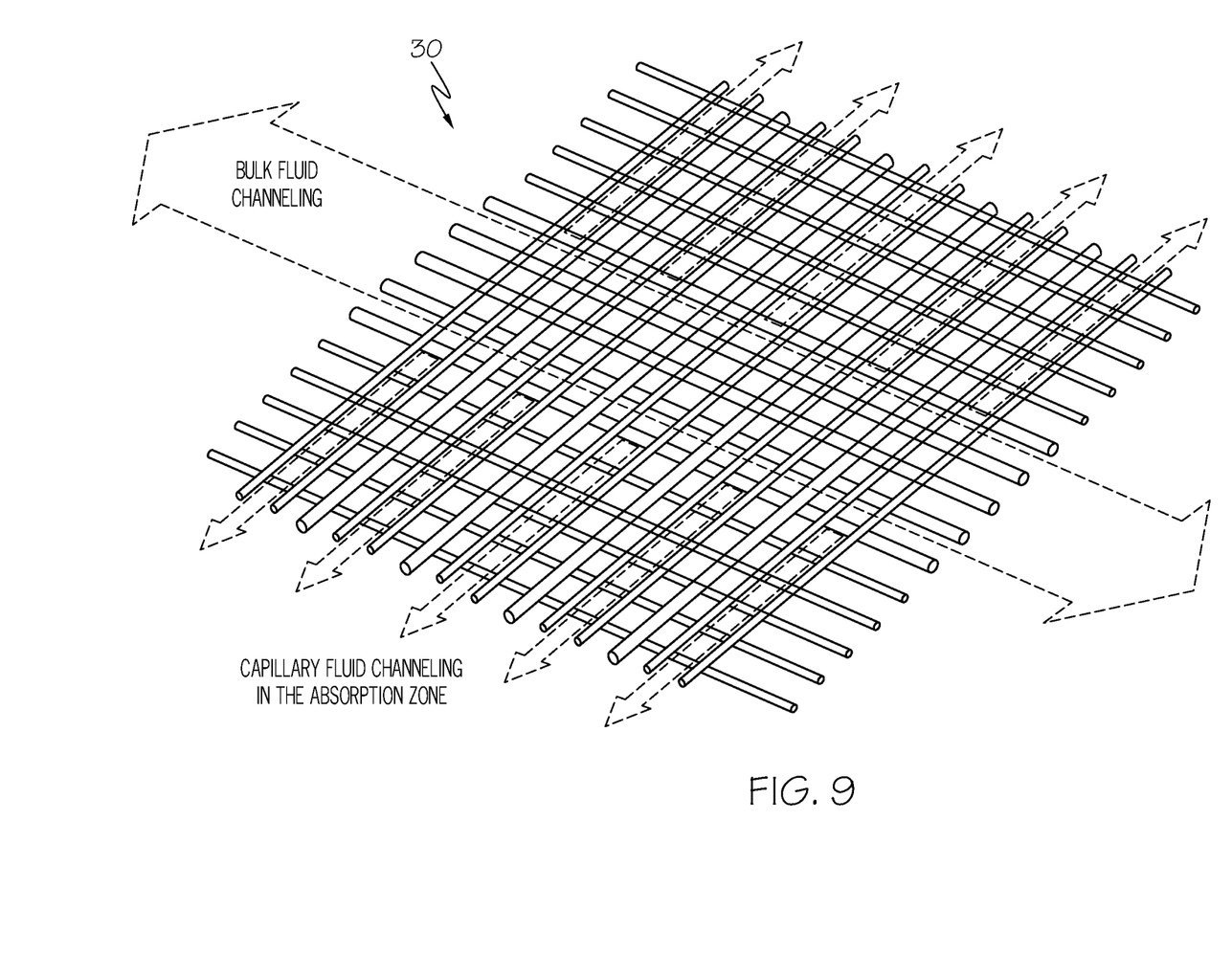
FIG. 9 is a schematic view illustrating bulk fluid channeling according to one or more embodiments of the present invention.

Moreover, the FIG. 8 design incorporates two superabsorbent polymer layers 20 sandwiched between three nylon flow media layers 50. Additionally, flow channels 25 are present in the top absorbent polymer layer corresponding to drainage slots or "through holes" in a mattress to further increase the wicking ability in those areas where large amounts of fluids would be introduced to the absorbent pad and tend to pool. These two modifications resulted in vastly superior absorbency performance in the AUL demonstration. In the demonstration, the modified absorbent pad exhibited both full absorption and even distribution of the fluid underneath the load plates in approximately one-third of the time it took a conventional pad as shown in FIG. 3 to absorb the same amount of fluid with no load at all as shown in FIG. 8.

The use of the FADE product highlighted the following performance characteristics: accelerated absorption rates; significantly more uniform fluid distribution and absorption; balanced drainage and channeling capabilities; and absorption under load that was nearly three times faster than superabsorbent polymer that was not under load.

It is further noted that terms like "preferably," "generally," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present disclosure.

It will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these aspects.

What is claimed is:

1. A fluid absorption and distribution enhancement (FADE) product comprising:
    at least two flow media layers; and
    at least one superabsorbent polymer layer sandwiched between the flow media layers.

2. The FADE product of claim 1 wherein the flow media layers comprise woven material, non-woven material, pressed mesh, knitted mesh, scrim material, or combinations thereof.

3. The FADE product of claim 1 wherein the flow media layers comprise of nylon, polypropylene, propylene ethylene copolymer, polyolefin, polyester, polyamide, polyvinyl chloride, polyurethane, or combinations thereof.

4. The FADE product of claim 1 further comprising superabsorbent fiber material.

5. The FADE product of claim 1 further comprising one or more flow channels in the superabsorbent polymer layer.

6. The FADE product of claim 1 wherein the superabsorbent polymer layer comprises poly (sodium acrylate) homopolymer or copolymer, polyacrylamide copolymer, ethylene maleic anhydride copolymer, polyvinyl alcohol copolymers, polyethylene oxide, polyacrylonitrile copolymer, cross-linked carboxymethylcellulose, or combinations thereof.

7. The FADE product of claim 1 further comprising at least two flow media layers in contact with one another.

8. The FADE product of claim 1 further comprising deionizing material or a deionizing coating.

9. The FADE product of claim 1 wherein the superabsorbent polymer layer comprises small slits configured to facilitate stretching.

10. The FADE product of claim 1 wherein the superabsorbent polymer layer comprises superabsorbent polymer impregnated into a stretchable fabric layer.

11. A stretcher comprising a body support frame and the fluid absorption and distribution enhancement product of claim 1.

12. The stretcher of claim 11 further comprising a mattress disposed over the fluid absorption and distribution enhancement product, the mattress comprising a plurality of drainage holes configured to allow bodily fluid flow through the drainage holes and into the fluid absorption and distribution enhancement product.

13. A method of enhancing fluid absorption and distribution enhancement under load comprising:
    providing a fluid absorption and distribution enhancement product under an applied load, wherein the fluid absorption and distribution enhancement product comprises at least two flow media layers, and at least one superabsorbent polymer layer comprising one or more flow channels extending therethrough, wherein the two flow media layers comprise an upper flow media layer and a lower flow media layer, and wherein the superabsorbent polymer layer is disposed between the upper flow media layer and lower flow media layer; and
    enhancing fluid distribution and fluid absorption in the superabsorbent polymer layer by draining fluid laterally by the upper flow media layer and through flow channels in the superabsorbent layer to the lower flow media layer.

14. The method of claim 13 wherein the superabsorbent polymer layer comprises poly (sodium acrylate) homopolymers or copolymers, polyacrylamide copolymers, ethylene maleic anhydride copolymers, polyvinyl alcohol copolymers, polyethylene oxides, polyacrylonitrile copolymers, cross-linked carboxymethylcellulose, or combinations thereof.

15. A fluid absorption and distribution enhancement (FADE) product comprising:
    at least three flow media layers including an upper flow media layer, a middle flow media layer, and a lower flow media layer; and
    at least two superabsorbent polymer layers comprising a first superabsorbent polymer layer disposed between the upper flow media layer and the middle flow media layer, and a second superabsorbent layer disposed between the middle flow media layer and the lower flow media layer.

16. The FADE product of claim 15 wherein the flow media layers comprise woven material, non-woven material, pressed mesh, knitted mesh, scrim material, or combinations thereof.

17. The FADE product of claim 15 wherein the flow media layers comprise of nylon, polypropylene, propylene ethylene copolymer, polyolefin, polyester, polyamide, polyvinyl chloride, polyurethane, or combinations thereof.

18. The FADE product of claim 15 further comprising one or more flow channels in the superabsorbent polymer layer.

19. The FADE product of claim 17 wherein the superabsorbent polymer layer comprises poly (sodium acrylate) homopolymer or copolymer, polyacrylamide copolymer, ethylene maleic anhydride copolymer, polyvinyl alcohol copolymers, polyethylene oxide, polyacrylonitrile copolymer, cross-linked carboxymethylcellulose, or combinations thereof.

20. A fluid absorption and distribution enhancement (FADE) product comprising:
    at least one flow media layer; and
    at least one superabsorbent polymer layer disposed above or below the flow media layer and comprising at least one flow channel.

* * * * *